(12) United States Patent
Lander et al.

(10) Patent No.: US 7,064,131 B2
(45) Date of Patent: Jun. 20, 2006

(54) COMPOUNDS AND METHODS FOR INHIBITING MRP1

(75) Inventors: Peter Ambrose Lander, Indianapolis, IN (US); Mark Christopher Lohman, Superior, CO (US)

(73) Assignee: Eli Lilly and Company, Indianapolis, IN (US)

( * ) Notice: Subject to any disclaimer, the term of this patent is extended or adjusted under 35 U.S.C. 154(b) by 32 days.

(21) Appl. No.: 10/473,218

(22) PCT Filed: Mar. 27, 2002

(86) PCT No.: PCT/US02/06664

§ 371 (c)(1),
(2), (4) Date: Jun. 25, 2004

(87) PCT Pub. No.: WO02/081481

PCT Pub. Date: Oct. 17, 2002

(65) Prior Publication Data

US 2004/0235880 A1 Nov. 25, 2004

Related U.S. Application Data

(60) Provisional application No. 60/282,643, filed on Apr. 9, 2001.

(51) Int. Cl.
*A61K 31/4402* (2006.01)
*A61K 31/4355* (2006.01)
*C07D 413/04* (2006.01)

(52) U.S. Cl. ..................... 514/293; 546/83

(58) Field of Classification Search .............. 546/83; 514/293
See application file for complete search history.

(56) References Cited

FOREIGN PATENT DOCUMENTS

| WO | WO99/51228 A | 10/1999 |
|---|---|---|
| WO | WO99/51236 | 10/1999 |
| WO | WO01/27116 | 4/2001 |

OTHER PUBLICATIONS

Wermuth, C.G., *Molecular Variations Based on Isosteric Replacements*, The Practise of Medicinal Chemistry, 1996, pp. 203-237.

*Primary Examiner*—Rita Desai
(74) *Attorney, Agent, or Firm*—Tina M. Tucker

(57) ABSTRACT

The present invention relates to a compound of formula (I) which are useful for inhibiting resistant neoplasms where the resistance is conferred in part or in total by MRP1.

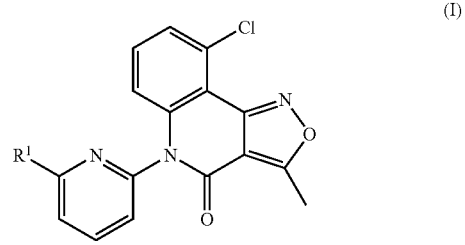

4 Claims, No Drawings

COMPOUNDS AND METHODS FOR INHIBITING MRP1

This application is a provisional of 60/282,643 filed Apr. 9, 2001.

Along with surgery and radiotherapy, chemotherapy continues to be an effective therapy for many cancers. In fact, several types of cancer, such as Hodgkin's disease, large cell lymphoma, acute lymphocytic leukemia, testicular cancer and early stage breast cancer, are now considered to be curable by chemotherapy. Other cancers such as ovarian cancer, small cell lung and advanced breast cancer, while not yet curable, are exhibiting positive response to combination chemotherapy.

One of the most important unsolved problems in cancer treatment is drug resistance. After selection for resistance to a single cytotoxic drug, cells may become cross resistant to a whole range of drugs with different structures and cellular targets, e.g., alkylating agents, antimetabolites, hormones, platinum-containing drugs, and natural products. This phenomenon is known as multidrug resistance (MDR). In some types of cells, this resistance is inherent, while in others, such as small cell lung cancer, it is usually acquired.

Such resistance is known to be multifactorial and is conferred by at least two proteins: the 170 kDa P-glycoprotein (MDR1) and the more recently identified 190 kDa multidrug resistance protein (MRP1). Although both MDR1 and MRP1 belong to the ATP-binding cassette superfamily of transport proteins, they are structurally very different molecules and share less than 15% amino acid homology. Despite the structural divergence between the two proteins, by 1994 there were no known consistent differences in the resistance patterns of MDR1 and MRP1 cell lines. However, the association, or lack thereof, of MRP1 and resistance to particular oncolytics is known. See Cole, et. al., "Pharmacological Characterization of Multidrug Resistant MRP-transfected Human Tumor Cells", *Cancer Research*, 54:5902–5910, 1994. Doxorubicin, daunorubicin, epirubicin, vincristine, paclitaxel, mitoxantrone, melphalan, and etoposide are substrates of MRP1, i.e., MRP1 can bind to these oncolytics and redistribute them away from their site of action, the nucleus, and out of the cell. Id. and Marquardt, D., and Center, M. S., *Cancer Research*, 52:3157, 1992.

Doxorubicin, daunorubicin, and epirubicin are members of the anthracycline class of oncolytics. They are isolates of various strains of *Streptomyces* and act by inhibiting nucleic acid synthesis. These agents are useful in treating neoplasms of the bone, ovaries, bladder, thyroid, and especially the breast. They are also useful in the treatment of acute lymphoblastic and myeloblastic leukemia, Wilm's tumor, neuroblastoma, soft tissue sarcoma, Hodgkin's and non-Hodgkin's lymphomas, and bronchogenic carcinoma.

Vincristine, a member of the vinca alkaloid class of oncolytics, is an isolate of a common flowering herb, the periwinkle plant (*Vinca rosea* Linn). The mechanism of action of vincristine is still under investigation but has been related to the inhibition of microtubule formation in the mitotic spindle. Vincristine is useful in the treatment of acute leukemia, Hodgkin's disease, non-Hodgkin's malignant lymphomas, rhabdomyosarcoma, neuroblastoma, and Wilm's tumor.

Etoposide, a member of the epipodophyllotoxin class of oncolytics, is a semisynthetic derivative of podophyllotoxin. Etoposide acts as a topoisomerase inhibitor and is useful in the therapy of neoplasms of the testis, and lung.

It is presently unknown what determines whether a cell line will acquire resistance via a MDR1 or MRP1 mechanism. Due to the tissue specificity of these transporters and/or in the case where one mechanism predominates or is exclusive, it would be useful to have a selective inhibitor of that one over the other. Furthermore, when administering a drug or drugs that are substrates of either protein, it would be particularly advantageous to coadminister an agent that is a selective inhibitor of that protein. It is, therefore, desirable to provide compounds that are selective inhibitors of MDR1 or MRP1.

The present invention relates to a compound of formula I:

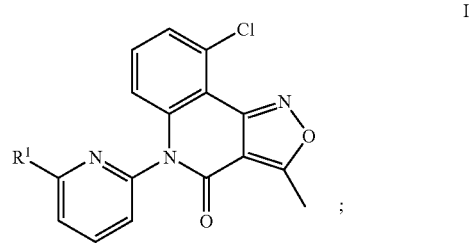

wherein:
R$^1$ is hydrogen, optionally substituted C$_1$–C$_4$ alkyl, (CH$_2$)$_n$C(O)R$^2$, (C$_1$–C$_4$ alkyl)NH$_2$, (CH$_2$)$_n$NHC(O)R$^3$, (optionally substituted C$_1$–C$_4$ alkyl)-optionally substituted phenyl, or optionally substituted heterocycle;

n is 0, 1, or 2;

p is 0, 1, 2, 3, or 4;

R$^2$ is C$_1$–C$_4$ alkoxy, (optionally substituted C$_1$–C$_4$ alkyl)-optionally substituted phenyl, (CH$_2$)$_p$-optionally substituted heterocycle, NHR$^4$, or (CH$_2$)$_p$-O-optionally substituted heterocycle;

R$^3$ is C$_1$–C$_4$ alkoxy, optionally substituted phenyl, (optionally substituted C$_1$–C$_4$ alkyl)-optionally substituted phenyl, or (CH$_2$)$_p$-optionally substituted heterocycle;

R$^4$ is (CH$_2$)$_p$-optionally substituted phenyl or (CH$_2$)$_p$-optionally substituted heterocycle; or a pharmaceutical salt thereof.

The present invention further relates to a method of inhibiting MRP1 in a mammal which comprises administering to a mammal in need thereof an effective amount of a compound of formula I, or a pharmaceutical salt thereof.

In another embodiment, the present invention relates to a method of inhibiting a resistant neoplasm, or a neoplasm susceptible to resistance in a mammal which comprises administering to a mammal in need thereof an effective amount of a compound of formula I, or a pharmaceutical salt thereof, in combination with an effective amount of an oncolytic agent.

Furthermore, this invention provides the use of a compound of Formula I for the manufacture of a medicament for the inhibition of MRP1. This invention also provides the use of a compound of Formula I for the manufacture of a medicament for the inhibition of a resistant neoplasm.

The present invention also relates to a pharmaceutical formulation comprising a compound of formula I, or a pharmaceutical salt thereof, in combination with one or more oncolytics, pharmaceutical carriers, diluents, or excipients therefor.

The current invention concerns the discovery that a select group of compounds, those of formula I, are selective inhibitors of multidrug resistant protein (MRP1) and are thus useful in treating MRP1 conferred multidrug resistance (MDR) in a resistant neoplasm and a neoplasm susceptible to resistance.

The terms "inhibit" as it relates to MRP1 and "inhibiting MRP1" refer to prohibiting, alleviating, ameliorating, halting, restraining, slowing or reversing the progression of, or reducing MRP1's ability to redistribute an oncolytic away from the oncolytic's site of action, most often the neoplasm's nucleus, and out of the cell.

As used herein, the term "effective amount of a compound of formula I" refers to an amount of a compound of the present invention which is capable of inhibiting MRP1. The term "effective amount of an oncolytic" refers to an amount of oncolytic capable of inhibiting a neoplasm, resistant or otherwise.

The term "inhibiting a resistant neoplasm, or a neoplasm susceptible to resistance" refers to prohibiting, halting, restraining, slowing or reversing the progression of, reducing the growth of, or killing resistant neoplasms and/or neoplasms susceptible to resistance.

The term "resistant neoplasm" refers to a neoplasm that is resistant to chemotherapy where that resistance is conferred in part, or in total, by MRP1. Such neoplasms include, but are not limited to, neoplasms of the bladder, bone, breast, lung(small-cell), testis, and thyroid and also includes more particular types of cancer such as, but not limited to, acute lymphoblastic and myeloblastic leukemia, Wilm's tumor, neuroblastoma, soft tissue sarcoma, Hodgkin's and non-Hodgkin's lymphomas, and bronchogenic carcinoma.

A neoplasm that is "susceptible to resistance" is a neoplasm where resistance is neither inherent nor currently present but can be conferred by MRP1 after chemotherapy begins. Thus, the methods of this invention encompass a prophylactic and therapeutic administration of a compound of formula I.

The term "chemotherapy" refers to the use of one or more oncolytics where at least one oncolytic is a substrate of MRP1. A "substrate of MRP1" is an oncolytic that binds to MRP1 and is redistributed away from the oncolytics site of action, (the neoplasm's nucleus) and out of the cell, thus, rendering the therapy less effective.

The terms "treat" or "treating" bear their usual meaning which includes preventing, prohibiting, alleviating, ameliorating, halting, restraining, slowing or reversing the progression, or reducing the severity of MRP1 derived drug resistance in a multidrug resistant tumor.

In the general formulae of the present document, the general chemical terms have their usual meanings. For example, the term "$C_1$–$C_4$ alkyl" refers to methyl, ethyl, propyl, isopropyl, cyclopropyl, butyl, cyclobutyl, s-butyl, and t-butyl. The term "$C_1$–$C_6$ alkyl" refers to a monovalent, straight, branched, or cyclic saturated hydrocarbon containing from 1 to 6 carbon atoms and includes $C_1$–$C_4$ alkyl groups. In addition, $C_1$–$C_6$ alkyl also includes, but is not limited to, cyclopentyl, pentyl, hexyl, cyclohexyl, and the like.

The term "optionally substituted $C_1$–$C_4$ alkyl" refers to a $C_1$–$C_4$ alkyl optionally substituted 1 time with a hydroxy group.

The terms "$C_1$–$C_4$ alkoxy" and "$C_1$–$C_6$ alkoxy" refer to moieties of the formula O—($C_1$–$C_4$ alkyl) and O—($C_1$–$C_6$ alkyl) respectively.

The term "halo" or "halide" refers to fluoro, chloro, bromo, and iodo.

The term "optionally substituted phenyl" refers to a phenyl ring optionally substituted 1 or 3 times independently with a $C_1$–$C_6$ alkyl, $C_1$–$C_4$ alkoxy, halo, benzyl, phenyl, trifluoromethyl, or an oxo group.

The term "heterocycle" refers to a monovalent, saturated, unsaturated, or aromatic mono cyclic or fused ring system of 5 to 7 total atoms respectively containing 1 to 3 heteroatoms selected independently from oxygen, sulfur, and nitrogen.

The term "optionally substituted heterocycle" refers to a heterocycle ring optionally substituted 1 or 2 times independently with a $C_1$–$C_6$ alkyl, $C_1$–$C_4$ alkoxy, halo, benzyl, phenyl, trifluoromethyl, or an oxo group.

The term "protecting group" (Pg) refers to an amino protecting group or a hydroxy protecting group. The species of protecting group will be evident from whether the "Pg" group is attached to a nitrogen atom (amino protecting group) or attached to an oxygen atom (hydroxy protecting group).

The term "amino protecting group" as used in this specification refers to a substituent(s) of the amino group commonly employed to block or protect the amino functionality while reacting other functional groups on the compound. Examples of such amino-protecting groups include the formyl group, the trityl group, the phthalimido group, the acetyl group, the trichloroacetyl group, the chloroacetyl, bromoacetyl, and iodoacetyl groups, urethane-type blocking groups such as benzyloxycarbonyl, 9-fluorenylmethoxycarbonyl ("FMOC"), and the like; and like amino protecting groups. The species of amino protecting group employed is not critical so long as the derivatized amino group is stable to the condition of subsequent reaction(s) on other positions of the molecule and can be removed at the appropriate point without disrupting the remainder of the molecule. Similar amino protecting groups used in the cephalosporin, penicillin, and peptide arts are also embraced by the above terms. Further examples of groups referred to by the above terms are described by T. W. Greene, "Protective Groups in Organic Synthesis", John Wiley and Sons, New York, N.Y., 1991, Chapter 7. This book shall hereafter be referred to as "Greene". A preferred amino protecting group is t-butyloxycarbonyl.

The term "hydroxy protecting group" denotes a group understood by one skilled in the organic chemical arts of the type described in Chapter 2 of Greene. Representative hydroxy protecting groups include, for example, ether groups including methyl and substituted methyl ether groups such as methyl ether, methoxymethyl ether, methylthiomethyl ether, tert-buylthiomethyl ether, (phenyldimethylsilyl) methoxy-methyl ether, benzyloxymethyl ether, p-methoxybenzyloxy-methyl ether, and tert-butoxymethyl ether; substituted ethyl ether groups such as ethoxyethyl ether, 1-(2-chloroethoxy)-ethyl ether, 2,2,2-trichloroethoxymethyl ether, and 2-(trimethylsilyl)ethyl ether; isopropyl ether groups; phenyl and substituted phenyl ether groups such as phenyl ether, p-chlorophenyl ether, p-methoxyphenyl ether, and 2,4dinitrophenyl ether; benzyl and substituted benzyl ether groups such as benzyl ether, p-methoxybenzyl ether, o-nitrobenzyl ether, and 2,6-dichlorobenzyl ether; and alkylsilyl ether groups such as trimethyl- triethyl- and triisopropylsilyl ethers, mixed alkylsilyl ether groups such as dimethylisopropylsilyl ether, and diethylisopropylsilyl ether; and ester protecting groups such as formate ester, benzylformate ester, mono-, di-, and trichloroacetate esters, phenoxyacetate ester, and p-chlorophenoxyacetate and the like. The species of hydroxy protecting group employed is not critical so long as the derivatized hydroxy group is stable to the conditions of subsequent reaction(s) on other positions of the intermediate molecule and can be selectively removed at the appropriate point without disrupting the remainder of the molecule including any other hydroxy protecting group(s).

In general, the term "pharmaceutical" when used as an adjective means substantially non-toxic to living organisms.

For example, the term "pharmaceutical salt" as used herein, refers to salts of the compounds of formula I which are substantially non-toxic to living organisms. See, e.g., Berge, S. M, Bighley, L. D., and Monkhouse, D. C., "Pharmaceutical Salts", *J. Pharm. Sci.,* 66:1, 1977. Typical pharmaceutical salts include those salts prepared by reaction of the compounds of formula I with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

The term "acid addition salt" refers to a salt of a compound of formula I prepared by reaction of a compound of formula I with a mineral or organic acid. For exemplification of pharmaceutical acid addition salts see, e.g., Berge, S. M, Bighley, L. D., and Monkhouse, D. C., *J. Pharm. Sci.,* 66:1, 1977. Since compounds of this invention can be basic in nature, they accordingly react with any of a number of inorganic and organic acids to form pharmaceutical acid addition salts.

The pharmaceutical acid addition salts of the invention are typically formed by reacting the compound of formula I with an equimolar or excess amount of acid. The reactants are generally combined in a mutual solvent such as diethylether, tetrahydrofuran, methanol, ethanol, isopropanol, benzene, and the like. The salts normally precipitate out of solution within about one hour to about ten days and can be isolated by filtration or other conventional methods.

Acids commonly employed to form acid addition salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, 1,5-naphthalene-disulfonate, naphthalene-1-sulfonate, naphthalene-2-sulfonate, mandelate and the like.

The term "base addition salt" refers to a salt of a compound of formula I prepared by reaction of a compound of formula I with a mineral or organic base. For exemplification of pharmaceutical base addition salts see, e.g., Berge, S. M, Bighley, L. D., and Monkhouse, D. C., *J. Pharm. Sci.,* 66:1, 1977. This invention also contemplates pharmaceutical base addition salts of compounds of formula I. The skilled artisan would appreciate that some compounds of formula I may be acidic in nature and accordingly react with any of a number of inorganic and organic bases to form pharmaceutical base addition salts. Examples of pharmaceutical base addition salts are the ammonium, lithium, potassium, sodium, calcium, magnesium, methylamino, diethylamino, ethylene diamino, cyclohexylamino, and ethanolamino salts, and the like of a compound of formula I.

While all of the compounds of the present invention are useful, certain of the compounds are particularly interesting and are preferred. The following listing sets out several groups of preferred compounds. It will be understood that each of the listings may be combined with other listings to create additional groups of preferred embodiments.
  a) $R^1$ is $(CH_2)_nC(O)R^2$;
  b) n is 0;
  c) $R^2$ is $NHR^4$, (optionally substituted $C_1$–$C_4$ alkyl)-optionally substituted phenyl or $(CH_2)_p$-optionally substituted heterocycle;
  d) p is 3;
  e) The compound is a pharmaceutical salt;
  f) The compound is the hydrochloride salt;
  g) The compounds of the Examples section;
  h) The method where the mammal is a human;
  i) The method where the oncolytic(s) is selected from: doxorubicin, daunorubicin, epirubicin, vincristine, and etoposide;
  j) The method where the neoplasm is of the Wilm's type, bladder, bone, breast, lung(small-cell), testis, or thyroid or the neoplasm is associated with acute lymphoblastic and myeloblastic leukemia, neuroblastoma, soft tissue sarcoma, Hodgkin's and non-Hodgkin's lymphomas, or bronchogenic carcinoma;
  k) The formulation where the oncolytic(s) is selected from the group: doxorubicin, daunorubicin, epirubicin, vincristine, and etoposide.

The compounds of the present invention can be prepared by a variety of procedures, some of which are illustrated in the Schemes below. The particular order of steps required to produce the compounds of formula I is dependent upon the particular compound being synthesized, the starting compound, and the relative lability of the substituted moieties.

Compounds of formula I may be prepared from compounds of formula II as illustrated in Scheme 1 below where $R^1$ is as described supra.

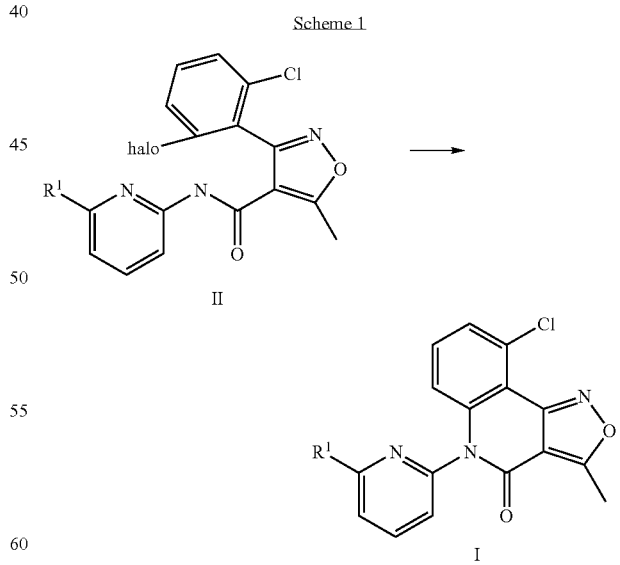

Compounds of formula I may be prepared by dissolving or suspending a compound of formula II in a suitable solvent, preferably dimethylformamide, and adding a suitable base, including potassium methoxide, potassium tert-butoxide, potassium bis(trimethylsilyl)amide, potassium carbonate, sodium hexamethyldisilazane, and potassium hexamethyldisilazane. The base is typically employed in a one to one ratio. However, as the skilled artisan would appreciate, a slight molar excess, usually in about a 1.1 to about a 3 fold molar excess relative to the compound of formula II, is acceptable.

The reactants are typically combined at a temperature from about 0° C. to about 100° C. The reactants are preferably combined at room temperature, and the resulting solution is typically mixed for from about 5 minutes to about 18 hours, preferably from about 5 minutes to about 1 hour.

Any protecting groups remaining in the cyclized compound of formula I may be removed as taught in Greene to provide additional compounds of formula L. Preferred choices of protecting groups and methods for their removal may be found in the Preparations and Examples sections below.

Where $R^1$ is as described supra, compounds of formula II may be prepared according to Scheme 2.

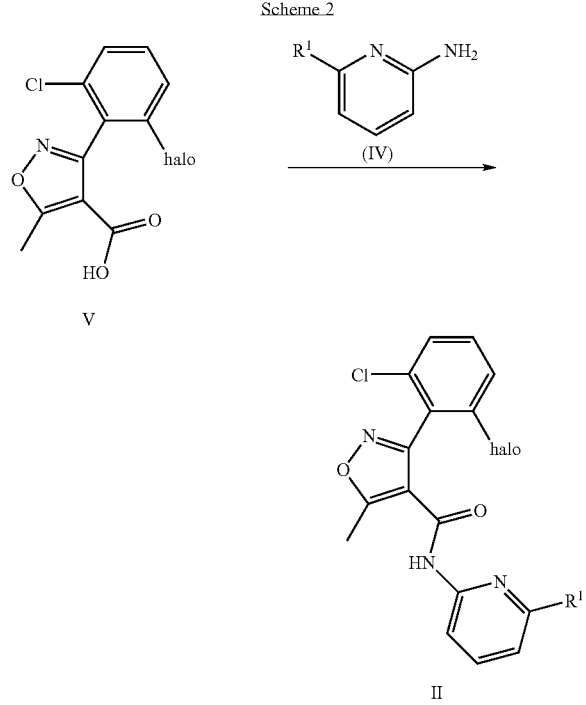

Scheme 2

Compounds of formula V may be converted to the corresponding acid halide by methods well known to one skilled in the art. Compounds of formula II may be prepared by dissolving or suspending an acid halide of a compound of formula V in a suitable solvent and adding a compound of formula IV in a suitable solvent. Triethylamine, N,N-diisopropylethyl amine, dichloromethane, dimethylformamide, and mixtures thereof are convenient solvents. This amide forming reaction is also preferably run in the presence of 4-dimethylaminopyridine (DMAP). The compound of formula V is preferably the corresponding carboxylic acid and is employed in an equimolar amount, relative to the compound of formula IV, but a slight excess (about a 0.05 to about 0.15 molar excess) is acceptable. DMAP is employed in a catalytic fashion. For example, about 5 molar percent to about 15 molar percent, relative to the compound of formula IV, is typically employed. A 10 molar percent is usually preferred.

Compounds of formula IV and V are well known in the art and to the extent not commercially available, are readily synthesized by standard procedures commonly employed in the art, see e.g. the Preparation section.

It should be recognized that the particular counterion forming a part of any salt of this invention is not of a critical nature, so long as the salt as a whole is pharmacologically acceptable and as long as the counterion does not contribute undesired qualities to the salt as a whole.

The optimal time for performing the reactions of Schemes 1–2 can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of formula I may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art. For example, the $R^1$ substituent of the compounds of formula IV may be a protecting group, which may be, removed during the synthesis of the compounds of formula I at any convenient point. The protecting group may be removed by methods well known in the art, see e.g. Greene, and $R^1$, $R^2$ and $R^3$ may be added through standard chemical techniques, see e.g. Larock, *Comprehensive Organic Transformations*, pgs. 785–820, 1640–1641, 1941–1949, and 1973–1976, VCH Publishers, New York, N.Y., 1999; and March J, *Advanced Organic Chemistry*, 1985, 3rd edition, page 377–378.

The following Preparations and Examples are provided to better elucidate the practice of the present invention and should not be interpreted in any way as to limit the scope of same. Those skilled in the art will recognize that various modifications may be made while not departing from the spirit and scope of the invention. All publications mentioned in the specification are indicative of the level of those skilled in the art to which this invention pertains. The terms and abbreviations used in the instant Preparations and Examples have their normal meanings unless otherwise designated. For example "°C.", "N", "mmol", "g", "mL", "M", "HPLC", "IR", "MS(FD)", "MS(IS)", "MS(FIA)", "MS (FAB)", "MS(EI)", "UV", and "$^1$H NMR", refer to degrees Celsius, normal or normality, millimole or millimoles, gram or grams, milliliter or milliliters, molar or molarity, high performance liquid chromatography, infra red spectrometry, field desorption mass spectrometry, ion spray mass spectrometry, flow injection analysis mass spectrometry, fast atom bombardment mass spectrometry, electron impact mass spectrometry, ultraviolet spectrometry, and proton nuclear magnetic resonance spectrometry respectively. In addition, the absorption maxima listed for the IR spectra are only those of interest and not all of the maxima observed.

Preparations

Preparation 1

(6-{[3-(2-Chloro-6-fluorophenyl)-5-methyl-isoxazole-4carbonyl]-amino}-pyridin-2-yl)-acetic acid ethyl ester Add $Et_3N$ (0.7 ml, 5.06 mmol) to a solution of ethyl 2-(2-Aminopyridin-6-yl)acetate (for preparation see Goto, Jiro; Sakane, Kazuo; Nakai, Yoshiharu; Teraji, Tsutomu; Kamiya, Takashi. *J. Antibiot.* (1984), 37(5), 532–45) (0.6 g, 3.33 mmol) and 3-(2-chloro-6-fluoro-phenyl)-5-methyl-isoxazole-4-carbonyl chloride (0.694 g, 2.53 mmol) in dichloromethane (7 ml) and stir overnight. Dilute the reaction with dichloromethane, wash ($H_2O$ then brine), dry ($MgSO_4$), filter, and concentrate. Column chromatography (silica gel, hexanes/EtOAc gradient) gives the title compound (0.81 g, 77%). Mass Spectrum (FIA) (m/z) 418.2 [M+1]

EXAMPLES

Example 1

[6-(9-Chloro-3-methyl-4oxo-5H-isoxazolo[4,3-c] quinolin-5-yl)-pyridin-2-yl]-acetic acid ethyl ester Add powdered $K_2CO_3$ (0.661 g, 4.8 mmol) to a solution of (6-{[3-(2-Chloro-6-fluorophenyl)-5-methyl-isoxazole-4-carbonyl]-amino}-pyridin-2-yl)-acetic acid ethyl ester (0.5 g, 1.2 mmol) in DMF (20 ml) under $N_2$ and stirred overnight. Dilute with EtOAc, wash ($H_2O$ then brine), dry ($MgSO_4$), filter, and concentrate. Column chromatography (silica gel, hexanes/EtOAc gradient) gives the title compound (0.376 g, 79%). Mass Spectrum (FIA) (m/z) 398.1 [M+1]

Example 2

[6-(9-Chloro-3-methyl-4-oxo-5H-isoxazolo[4,3-c] quinolin-5-yl)-pyridin-2-yl]-acetic acid Heat [6-(9-Chloro-3-methyl-4-oxo-5H-isoxazolo[4,3-c] quinolin-5-yl)-pyridin-2-yl]-acetic acid ethyl ester (0.359 g, 0.9 mmol), MeOH (4.5 ml), THF (0.5ml), and 1N NaOH (1.8 ml, 1.8 mmol) at 50° C. for 2 h. Cool to room temperature, dilute with $H_2O$, and acidify (conc. HCl) to less than pH 3. Extract with EtOAc twice and wash the combined extracts ($H_2O$ then brine), dry ($MgSO_4$), filter, and concentrate giving the title compound (0.338 g, 100%). Use this material without further purification. Mass Spectrum (FIA) (m/z) 370.0 [M+1]

Example 3

2-[6-(9-Chloro-3-methyl-4-oxo-5H-isoxazolo[4,3-c] quinolin-5-yl)-pyridin-2-yl]-N-(3,4,5-trimethoxyphenyl)-acetamide Add EDCI (0.016 g, 0.08 mmol), 3,4,5-trimethoxyaniline (0.014 g, 0.075 mmol), and DMAP (0.001 g, 0.01 mmol) to a solution of [6-(9-Chloro-3-methyl-4-oxo-5H-isoxazolo[4,3]quinolin-5-yl)-pyridin-2-yl]-acetic acid (0.02 g, 0.05 mmol) in dichloromethane (1.25 ml) and DMF (0.5 ml). Stir overnight. Dilute with dichloromethane, wash (1.0 N HCl, $H_2O$, brine), dry ($MgSO_4$), filter, and concentrate. Column chromatography (silica gel, acetone/dichloromethane gradient) gives the title compound (0.024 g, 90%). Mass Spectrum (EIA) (m/z) 535.2 [M+1]

Example 4

2-[6-(9-Chloro-3-methyl-4-oxo-5H-isoxazolo[4,3-c] quinolin-5-yl)-pyridin-2-yl]-N-(2-methoxy-5-nitrophenyl)-acetamide

[6-(9-Chloro-3-methyl-4-oxo-5H-isoxazolo[4,3-c]quinolin-5-yl)-pyridin-2-yl]-acetic acid (0.075 g, 0.2 mmol), EDCI (0.055 g, 0.3 mmol), 2-Nitro-5-methoxyaniline (0.044 g, 0.26 mmol), DMAP (0.005 g, 0.04 mmol) in dichloromethane (4.5 ml) and DMF (0.75 ml) react for 5 h in a fashion similar to that of Example 3. Column chromatography (silica gel, acetone/dichloromethane gradient) gives the title compound (0.012 g, 12%). Mass Spectrum (FIA) (m/z) 520.2 [M+1]

Example 5

2-[6-(9-Chloro-3-methyl-4-oxo-5H-isoxazolo[4,3-c] quinolin-5-yl)-pyridin-2-yl]-N-(3-methoxyphenyl)-acetamide

[6-(9-Chloro-3-methyl4-oxo-5H-isoxazolo[4,3-c]quinolin-5-yl)-pyridin-2-yl]-acetic acid (0.075 g, 0.2 mmol), EDCI (0.055 g, 0.3 mmol), 3-methoxyaniline (0.03 ml, 0.26 mmol), DMAP (0.005 g, 0.04 mmol) in dichloromethane (4.5 ml) and DMP (0.75 ml) react for 5.5 h in a fashion similar to that of Example 3. Column chromatography (silica gel, acetone/dichloromethane gradient) gives the title compound (0.05 g, 53%).

Mass Spectrum (FIA) (m/z) 473.1 [M−1]

Example 6

2-[6-(9-Chloro-3-methyl-4-oxo-5H-isoxazolo[4,3-c] quinoln-5-yl)-pyridin-2-yl]-N-(3-nitrophenyl)-acetamide

[6-(9-Chloro-3-methyl-4-oxo-5H-isoxazolo[4,3-c]quinolin-5-yl)-pyridin-2-yl]-acetic acid (0.075 g, 0.2 mmol), EDCI (0.055 g, 0.3 mmol), 3-nitroaniline (0.036 g, 0.26 mmol), DMAP (0.005 g, 0.04 mmol) in dichloromethane (4.5 ml) and DNT (0.75 ml) react for 5.5 h in a fashion similar to that of Example 3. Column chromatography (silica gel, acetonel/dichloromethane gradient) gives the title compound (0.024 g, 24%). Mass Spectrum (FIA) (m/z) 488.1 [M−1]

The compounds of the invention are inhibitors of MRP1. Thus, the compounds of the invention may be used to inhibit any neoplasm having intrinsic and/or acquired resistance, conferred in part or in total by MRP1, to an oncolytic or oncolytics. In other words, treatment of such a neoplasm with an effective amount of a compound of this invention will cause the neoplasm to be more sensitive to chemotherapy that was rendered less efficacious by MRP1.

Vincristine, epirubicin, daunorubicin, doxorubicin, and etoposide are examples of oncolytics that are substrates of MRP1. See Cole, et. al., "Pharmacological Characterization of Multidrug Resistant MRP-transfected Human Tumor Cells", *Cancer Research,* 54:5902–5910, 1994. Since MRP1 is ubiquitous in mammals, particularly humans, Nooter, K, et. al., "Expression of the Multidrug Resistance-Associated Protein (MRP) Gene in Human Cancers", *Clin. Can. Res.*, 1:1301–1310, (1995), chemotherapy whose goal is to inhibit a neoplasm employing any of those agents has the potential to be rendered less efficacious by MRP1. Thus, neoplasms of the bladder, bone, breast, lung(small-cell), testis, and thyroid and more specific types of cancer such as acute lymphoblastic and myeloblastic leukemia, Wilm's tumor, neuroblastoma, soft tissue sarcoma, Hodgkin's and non-Hodgkin's lymphomas, and bronchogenic carcinoma may be inhibited with a combination of one or more of the above oncolytics and a compound of this invention.

The biological activity of the compounds of the present invention was evaluated employing an initial screening assay, which rapidly and accurately measured the activity of the tested compound in inhibiting MRP1 or MDR1. Assays useful for evaluating this reversing capability are well known in the art. See, e.g., T. McGrath, et al., *Biochemical Pharmacology*, 38:3611, 1989; D. Marquardt and M. S. Center, *Cancer Research*, 52:3157, 1992; D. Marquardt, et al., *Cancer Research*, 50:1426, 1990; and Cole, et. al., *Cancer Research*, 54: 5902–5910, 1994.

Assay for Reversal of MRP1-Mediated Doxorubicin Resistance and MDR1-Mediated Vincristine Resistance: HL60/ADR and HL60/VCR are continuous cell lines, which were selected for doxorubicin and vincristine resistance respectively by culturing HL60, a human acute myeloblastic leukemia cell line, in increasing concentrations of doxorubicin or vincristine until a highly resistant variant was attained.

HL60/ADR and HL60/VCR cells were grown in RPMI 1640 (Gibco) containing 10% fetal bovine serum (FBS) and 250 µg/ml GENTAMICIN™ (Sigma). Cells were harvested; washed twice with assay medium (same as culture media); counted; and diluted to $2 \times 10^5$ cells/ml in assay medium. Fifty microliters of cells were aliquoted into wells of a 96 well tissue culture plate. One column of each 96 well plate served as a negative control and received assay medium containing no cells.

Test compounds and reference compounds were dissolved in dimethyl sulfoxide (DMSO) at a concentration of 5 mM. Samples were diluted to 20 µM in assay medium and 25 µl of each test compound was added to 6 wells. Assay standards were run in quadruplicate. Twenty-five microliters of 0.4% DMSO was added to four wells as a solvent control. Assay media was added to all wells to achieve a final volume of 100 µl per well.

The plates were incubated at 37° C. for 72 hours in a humidified incubator with a 5% carbon dioxide atmosphere. Cell viability and vitality was measured by oxidation of a tetrazolium salt using standard conditions. The plates were incubated for 3 hours at 37° C. Absorbance was determined at 490 nm using a microtitre plate reader.

The ability of a test compound to reverse the resistance of HL60/ADR and HL60/VCR cells to doxorubicin was determined by comparison of the absorbance of the wells containing a test compound in addition to the oncolytic (doxorubicin) with the absorbance of wells containing the oncolytic without a test compound. Controls were used to eliminate background and to ensure the results were not artifactual. The results of the assay are expressed as percent inhibition of cell growth. The oncolytic alone at the tested concentration does not usually inhibit the growth of HL60/ADR or HL60/VCR cells.

Representative compounds of formula I demonstrated a significant effect in reversing the MRP1 multiple drug resistance. Many of the compounds showed very significant enhancement of activity in combination with the oncolytic agent as opposed to the oncolytic agent alone. In addition, a large majority of the compounds tested displayed a significant degree of selective inhibition of the HL60/ADR cell line over the HL60/VCR cell line.

When administering an oncolytic in practicing the methods of this invention, the amount of oncolytic employed will be variable. It should be understood that the amount of the oncolytic actually administered will be determined by a physician, in the light of the relevant circumstances, including the condition to be treated, the chosen route of administration, the actual oncolytic administered, the age, weight, and response of the individual patient (mammal), and the severity of the patient's symptoms. Of course, the amount of oncolytic administered should be decided and closely monitored by that patient's physician. After deciding on the oncolytic or oncolytics to employ, "The Physician's Desk Reference®", published by Medical Economics Company at Montvale, N.J. 07645–1742, is a helpful resource to the physician in deciding on amounts of the oncolytic to administer and is updated annually.

Preferred formulations, and the methods of this invention employing those formulations, are those which do not contain an oncolytic. Thus, it is preferred to administer the compounds of this invention separately from the oncolytic. The oncolytics mentioned in this specification are commercially available and may be purchased in pre-formulated forms suitable for the methods of this invention.

The compounds of formula I alone, or optionally in combination with an oncolytic, are usually administered in the form of pharmaceutical formulations. These formulations can be administered by a variety of routes including oral, rectal, transdermal, subcutaneous, intravenous, intramuscular, and intranasal. Such formulations are prepared in a manner well known in the pharmaceutical art and comprise at least one active compound of formula I.

The present invention also includes methods employing pharmaceutical formulations, which contain, as the active ingredient, the compounds of formula I, and optionally an oncolytic, associated with pharmaceutical carriers. In making the formulations of the present invention the active ingredient(s) is usually mixed with an excipient, diluted by an excipient, or enclosed within such a carrier which can be in the. form of a capsule, sachet, paper or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound(s) to provide the appropriate particle size prior to combining with the other ingredients. If the active compound(s) is substantially insoluble, it ordinarily is milled to a particle size of less than 200 mesh. If the active compound(s) is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The formulations of the invention can be formulated so as to provide quick, sustained or delayed release of the active ingredient after administration to the patient by employing procedures known in the art.

The formulations are preferably formulated in a unit dosage form, each dosage containing from about 5 to about 100 mg, more usually about 10 to about 30 mg, of each active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The compounds of formula I are effective over a wide dosage range. For example, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

For preparing solid formulations such as tablets, the principal active ingredient(s) is mixed with a pharmaceutical excipient to form a solid preformulation composition containing a homogeneous mixture of a compound of the present invention. When referring to these preformulation compositions as homogeneous, it is meant that the active ingredient(s) is dispersed evenly throughout the formulation so that the formulation may be readily subdivided into equally effective unit dosage forms such as tablets, pills and capsules. This solid preformulation is then subdivided into unit dosage forms of the type described above containing from 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The novel formulations which are liquid forms may be incorporated for administration orally or by injection and include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Formulations for inhalation or insufflation include solutions and suspensions in pharmaceutical, aqueous or organic solvents, or mixtures thereof, and powders. The liquid or solid formulations may contain suitable pharmaceutical excipients as described supra. Preferably the formulations are administered by the oral or nasal respiratory route for local or systemic effect. Compositions in preferably pharmaceutical solvents may be nebulized by use of inert gases.

Nebulized solutions may be breathed directly from the nebulizing device or the nebulizing device may be attached to a face mask, tent, or intermittent positive pressure breathing machine. Solution, suspension, or powder formulations may be administered, preferably orally or nasally, from devices, which deliver the formulation in an appropriate manner.

The following formulation examples are illustrative only and are not intended to limit the scope of the invention in any way. "Active ingredient(s)" means a compound according to formula I or a pharmaceutical salt thereof optionally with one or more oncolytics.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical formulation to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions, which can transiently open the blood-brain barrier.

What is claimed is:

1. A compound of formula I:

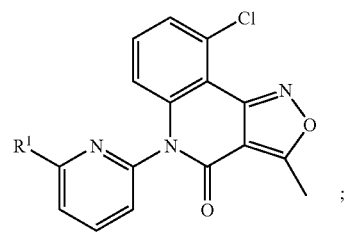

wherein:
R$^1$ is hydrogen,
C$_1$–C$_4$ alkyl optionally substituted 1 time with a hydroxy group,
(CH$_2$)$_n$C(O)R$^2$, (C$_1$–C$_4$ alkyl)NH2, (CH$_2$)$_n$NHC(O)R$^3$,
(C$_1$–C$_4$ alkyl optionally substituted 1 time with a hydroxy group)-phenyl optionally substituted 1 or 3 times independently with a C$_1$–C$_6$ alkyl, C$_1$–C$_4$ alkoxy, halo, benzyl, phenyl, trifluoromethoxy, nitro, or an oxo group, or
n is 0, 1, or 2;
p is 0, 1, 2, 3, or 4;

$R^2$ is $C_1$–$C_4$ alkoxy, hydroxy, ($C_1$–$C_4$ alkyl optionally substituted 1 time with a hydroxy group)-phenyl optionally substituted 1 or 3 times independently with a $C_1$–$C_6$ alkyl, $C_1$–$C_4$ alkoxy, halo, benzyl, phenyl, trifluoromethoxy, nitro, or an oxo group;

$NHR^4$, or $R^3$ is $C_1$–$C_4$ alkoxy, phenyl optionally substituted 1 or 3 times independently with a $C_1$–$C_6$ alkyl, $C_1$–$C_4$ alkoxy, halo, beazyl, phenyl, trifluoromethoxy, nitro, or an oxo group, ($C_1$–$C_4$ alkyl optionally substituted 1 time with a bydroxy group)-phenyl optionally substituted 1 or 3 times independently with a $C_1$–$C_6$ alkyl, $C_1$–$C_4$ alkoxy, halo, benzyl, phenyl, trifluoromethoxy, nitro, or an oxo group, or $R^4$ is $(CH_2)_p$-phenyl optionally substituted 1 or 3 times independently with a $C_1$–$C_6$ alkyl, $C_1$–$C_4$ alkoxy, halo, benzyl, phenyl, trifluoromethoxy, nitro, or an oxo group, or or a pharmaceutical salt thereof.

2. A method of reducing the severity of MRP1 derived drug resistance of one or more oncolvtic agents selected from the group consisting of vincristine, epirubicin, daunorubucin, doxorubicin, and etoposide which comprises administering to a mammal in need thereof an MRP1 inhibitory effective amount of a compound of claim 1.

3. A method of reducing the severity of MRP1 derived drug resistsnce in a neoplasm susceptible to resistance, selected from the group consisting of neoplasms of the bladder, neoplasms of the bone, neoplasms of the breast, neoplasms of the small-cell lung, neoplasms of the testis, neoplasms of the thyroid, acute lymphoblastic leukemia, in a mammal which comprises administering to a mammal in need thereof an MRP1 inhibitory effective amount of a compound of claim 1 in combination with an effective amount of one or more oncolytic agents selected from the group consisting of vincristine, epirubicin, daunorubucin, doxorubicin, and etoposide.

4. A pharmaceutical formulation comprising a compound of claim 1 or a pharmaceutical salt thereof in combination with one or more pharmaceutical carriers, diluents, or excipients therefor.

* * * * *